United States Patent [19]

Barriere et al.

[11] Patent Number: 4,775,753
[45] Date of Patent: Oct. 4, 1988

[54] NEW PROCESS FOR THE PREPARATION OF PRISTINAMYCIN $II_B$ DERIVATIVES

[75] Inventors: Jean-Claude Barriere, Massy; Jean-Pierre Bastart, Lesigny; Jean-Marc Paris, Vaires sur Marne, all of France

[73] Assignee: Rhone-Poulenc Sante, Courbevoie, France

[21] Appl. No.: 70,389

[22] Filed: Jul. 7, 1987

[51] Int. Cl.$^4$ ............... C07D 498/14; A61K 31/42
[52] U.S. Cl. ........................... 540/456; 540/455
[58] Field of Search ..................... 540/456, 455

[56] References Cited

U.S. PATENT DOCUMENTS 2,802,722  8/1957  Stephanou ............... 423/515
4,668,669  5/1987  Barriere et al. ........... 540/455

OTHER PUBLICATIONS

Bloch et al., "J. Org. Chem.", vol. 50, (1985), pp. 1544-1545.
Trost et al., "J. Org. Chem.", vol. 53, (1988), pp. 532-537.
Kennedy et al., J. Org. Chem., (1960), 25, 1901-1905.
Trost et al., Tetrahedron Letters, 22, (1981), 1287-1290.

Primary Examiner—Robert T. Bond
Attorney, Agent, or Firm—Stevens, Davis, Miller & Mosher

[57] ABSTRACT

Pristinamycin $II_B$ derivatives of formula I in which R represents:

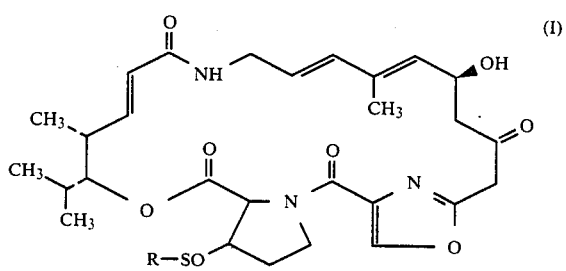

either a 4- to 7-membered nitrogen-containing heterocyclic radical, optionally containing 1 or more other hetero atoms chosen from nitrogen, oxygen and sulphur in the sulphoxide or sulphone form, and unsubstituted or substituted by alkyl, or alkyl of 2 to 4 carbon atoms, substituted by 1 or 2 radicals chosen from phenyl, cycloalkylamino or N-alkyl-N-cycloalkylamino having 3 to 6 ring carbon atoms, alkylamino, dialkylamino or dialkylcarbamoyloxy (the alkyl parts of these last 2 radicals being optionally joined to form, with the nitrogen atom to which they are attached, a 4- to 7-membered saturated or unsaturated heterocycle optionally containing another hetero atom chosen from nitrogen, oxygen and sulphur in the sulphoxide or sulphone form, and unsubstituted or substituted by alkyl) or a said alkyl substituted by one or more 4- or 7-membered nitrogen-containing heterocycles optionally containing 1 or 2 other hetero atoms chosen from nitrogen, oxygen and sulphur in the sulphoxide or sulphone form and unsubstituted or substituted by an alkyl radical, the said heterocycles being attached to the alkyl via a carbon atom, at least one of the substituents carried by the alkyl being a nitrogen-containing substituent capable of forming salts, or a [(S)-1-methyl-2-pyrrolidinyl]methyl radical, the aforesaid alkyl radicals being straight-chain or branched and containing, unless otherwise stated, 1 to 10 carbon atoms each, including isomeric forms thereof and mixtures thereof, and the salts thereof, are made by oxidizing a pristinamycin $II_B$ derivative of formula II

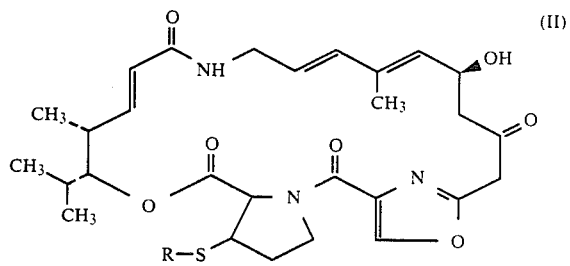

with potassium peroxymonosulphate.

3 Claims, No Drawings

NEW PROCESS FOR THE PREPARATION OF PRISTINAMYCIN II$_B$ DERIVATIVES

The present invention relates to the preparation of pristinamycin II$_B$ S-oxides.

European Patent Application No. 191,662 describes inter alia pristinamycin II$_B$ S-oxides of formula:

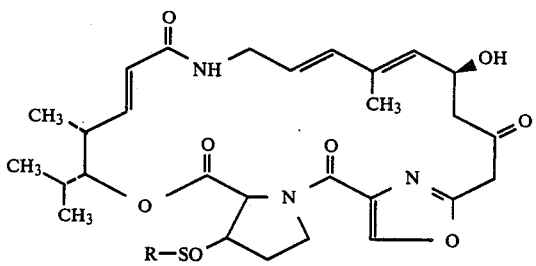

(I)

in which the symbol R represents
either a 4- to 7-membered nitrogen-containing heterocyclic radical, optionally containing 1 or more other hetero atoms chosen from nitrogen, oxygen and sulphur in the sulphoxide or sulphone form, and unsubstituted or substituted by alkyl,
or alkyl of 2 to 4 carbon atoms, substituted by 1 or 2 radicals chosen from phenyl, cycloalkylamino or N-alkyl-N-cycloalkylamino having 3 to 6 ring carbon atoms, alkylamino, dialkylamino or dialkylcarbamoyloxy (the alkyl parts of these last 2 radicals being optionally joined to form, with the nitrogen atom to which they are attached, a 4- to 7-membered saturated or unsaturated heterocycle optionally containing another hetero atom chosen from nitrogen, oxygen and sulphur in the sulphoxide or sulphone form, and unsubstituted or substituted by alkyl) or a said alkyl substituted by one or more 4- to 7-membered nitrogen-containing heterocycles optionally containing 1 or 2 other hetero atoms chosen from nitrogen, oxygen and sulphur in the sulphoxide or sulphone form and unsubstituted or substituted by an alkyl radical, the said heterocycles being attached to the alkyl via a carbon atom, at least one of the substituents carried by the alkyl being a nitrogen-containing substituent capable of forming salts,
or a [(S)-1-methyl-2-pyrrolidinyl]methyl radical, the aforesaid alkyl radicals being straight-chain or branched and containing, unless otherwise stated, 1 to 10 carbon atoms each, including isomeric forms thereof and mixtures thereof, and the acid addition salts thereof.

In formula I, when R represents a heterocyclic radical, this radical can be, for example, chosen from 3-azetidinyl, 3-pyrrolidinyl, 3-or 4-piperidyl, or 3-or 4-azepinyl. When R represents a heterocyclylalkyl radical, the heterocyclic radical can be chosen, for example, from the aforesaid radicals or 2-azetidinyl, 2-pyrrolidinyl, 2-piperidyl, 2-azepinyl, piperazinyl, 4-alkyl-piperazinyl, quinolyl, isoquinolyl, or imidazolyl. When R contains a dialkylamino or dialkylcarbamoyloxy radical in which the alkyl residues are joined to form with the nitrogen atom to which they are attached a heterocyclic ring, the latter can be chosen, for example, from 1-azetidinyl, 1-pyrrolidinyl, piperidino, 1-azepinyl, morpholino, thiomorpholino in the sulfoxide or sulphone form, 1-piperazinyl, 4-alkyl 1-piperazinyl, N-alkyl 1-homopiperazinyl, or 1-imidazolyl.

It has now been found that the products of formula (I) may advantageously be obtained by oxidizing a pristinamycin II$_B$ derivative (or a salt or protected derivative thereof) of formula:

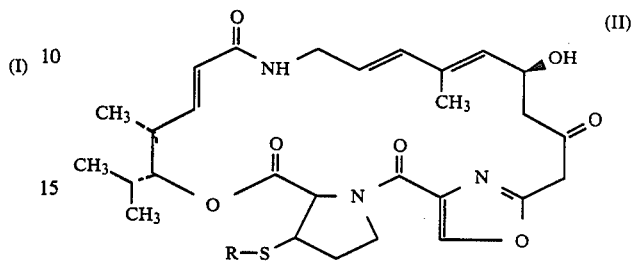

(II)

in which R is defined as above, it being understood that where R contains a sulphur-containing heterocycle, the sulphur atom may be in the form of sulphide, sulphoxide or sulphone, with potassium peroxymonosulphate, and optionally separating the isomers obtained.

Potassium peroxymonosulphate is sold commercially, under the trade mark "Oxone", in the form of a mixture which also contains potassium sulphate and potassium hydrogen sulphate, produced as described in U.S. Pat. No. 2,802,722, and references herein to potassium peroxymonosulphate are to be understood to include reference to this material. A slight stoichiometric excess of the potassium peroxymonosulphate is preferably used in relation to the starting material of formula II, account being taken of the purity of the potassium peroxymonosulphate and the number of oxidizable sulphur atoms in the starting material.

The reaction may be carried out in an aqueous medium, e.g. water, or a water/alcohol (e.g. water/methanol) or water/chlorinated solvent (e.g. water/dichloromethane) mixture, at usually a temperature between $-60°$ and $+25°$ C.

When the pristinamycin II$_B$ derivative of formula (II) is employed in the form of a salt, a salt formed with an organic or inorganic acid and preferably with trifluoroacetic, tartaric, acetic, benzoic, hydrochloric or sulfuric acid or with potassium hydrogen sulfate may be used.

When R contains an alkylamino or cycloalkylamino substituent, it is possible to employ a protected derivative of the starting material of formula (II). The latter may be protected by any amine-protecting group, the attachment and the removal of which does not affect the rest of the molecule. The trifluoroacetyl group, which can be removed by a reaction involving treatment with an alkali metal bicarbonate (sodium or potassium bicarbonate) in an aqueous solution, is advantageously used.

The potassium peroxymonosulphate may be prepared according to the method described in U.S. Pat. No. 2, 802,722.

The starting material of formula (II) may be obtained by the method described in European Patent Application No. 191,662. It is not absolutely essential to isolate the pristinamycin II$_B$ derivative of formula (II) in pure form in order to implement the process of the invention.

The products of formula (I) obtained at the end of this process may be purified by known methods, e.g. by crystallization, chromatography or successive extractions in an acid or basic medium. Since synergistins are sensitive to alkaline media, "basic medium" means in this context a medium of which the alkalinity is just sufficient to release the parent substance from its addition salt with an acid, i.e. a medium having a pH not exceeding 8.

The isomers of the products of formula (I) may be separated by any known method. This is advantageously carried out by chromatography or high performance liquid chromatography.

The products of formula (I) obtained by the process of the invention show an antibacterial activity on gram-positive bacteria (of the Staphylococcus, Streptococcus, Pneumococcus and Enterococcus type) and gram-negative bacteria (of the Haemophilus, Gonococcus and Meningococcus type). Additionally, they have the advantage that they can be dissolved in water generally as salts, at usable therapeutic doses and that they enhance, by a synergistic phenomenon, the antibacterial action of pristinamycin $I_A$, virginiamycin S or their soluble derivatives as described in European Patent Application No. 191,662.

Additionally, the products of formula (I) obtained by the process of the invention may be used in the preparation of sulphones derived from pristinamycin $II_B$, of general formula:

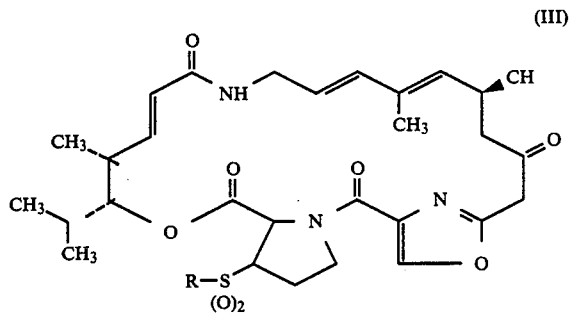

(III)

is as defined in the case of formula (I), which are active as antimicrobial agents and also have the property of synergizing the action of group I pristinamycins.

The sulphones derived from pristinamycin $II_B$ of formula (III) may be prepared by oxidizing a pristinamycin $II_B$ derivative of formula (I), under the conditions described in European Patent Application No. 191,662.

The process of the invention has the advantage that it can be implemented easily and that it facilitates the production of a purer product, which is easier to treat, when appropriate, in the subsequent phase of preparing the corresponding sulphone, and that it involves fewer risks of the starting material being degraded and especially fewer risks in carrying out the preparation of the products of formula (I).

More particularly, the process of the invention makes it possible to produce compounds of formula I in which the symbol R represents alkyl of 2 to 4 carbon atoms substituted by one or two radicals chosen from phenyl, cycloalkylamino, or N-alkyl-N- cycloalkylamino containing 5 or 6 ring atoms, alkylamino of 1 to 4 carbon atoms, dialkylamino (in which each alkyl contains 1 to 3 carbon atoms or the alkyls are joined to form with the nitrogen atoms to which they are attached a saturated heterocyclic ring of 5 or 6 ring atoms), or represents a nitrogen-containing heterocyclic radical or 5 or 6 ring atoms which is unsubstituted or substituted by alkyl of 1 to 4 carbon atoms, it being understood that at least one of the substituents carried by the aforesaid alkyl chain is a nitrogen-containing substituent capable of forming salts and that at least one of the radicals carried by this chain is in the 1 or 2 position.

The products of formula (I) obtained by the new process may be converted into salts. Suitable pharmaceutically acceptable salts include especially the addition salts with inorganic acids such as hydrochlorides, hydrobromides, sulphates, nitrates and phosphates, or with organic acids, such as acetates, propionates, succinates, maleates, fumarates, methanesulphonates, p-toluenesulphonates, isethionates, citrates and tartrates or substitution derivatives of these compounds.

The following Examples illustrate the invention. The NMR spectra for the products described in these Examples have general characteristics which are common to all the products of formula (I) and particular characteristics which are specific to each of the products depending on the substituents. Only the specific characteristics due to the radicals which vary are mentioned in the Examples. In the products of formula (I), all the protons are denoted according to the numbering shown in the following formula:

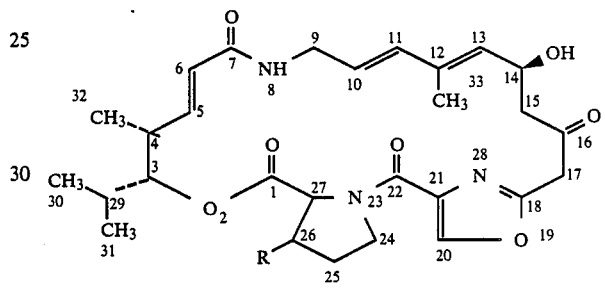

Unless otherwise stated, all the spectrum determinations were carried out at 250 MHz in deuterochloroform; the chemical shifts are expressed in ppm relative to the tetramethyl silane signal. The abbreviations used below are as follows:

s=singlet
d=doublet
t=triplet
m=multiplet
c=complex
dd=doublet of doublet
dt=doublet of triplet
ddd=doublet of doublet of doublet
dddd=doublet of doublet of doublet of doublet It is understood that the different isomers were classified arbitrarily according to the chemical shifts observed in NMR spectroscopy.

The isomers with the following characteristics are called isomer $A_1$ and isomer $A_2$ of the products of general formula (I):
approximately 1.7 (s, —$CH_3$ at 33) ; approximately 3.8 (s, >$CH_2$ at 17) ; <5 (d, -$H_{27}$) isomer $A_2$ or >5 (d, -$H_{27}$) isomer $A_1$; approximately 5.50 (broad d, -$H_{13}$) ; approximately 6.20 (d, -$H_{11}$); approximateLy 6.6 ($\geq$NH at 8) ; $\geq$8 (s, -$H_{20}$).

The isomers with the following characteristics are called isomer $B_1$ and isomer $B_2$ of the products of general formula (I):
approximately 1.5 (s, -$CH_3$ at 33) ; approximately 3.7 and 3.9 (2d, >$CH_2$ at 17) ; approximately 4.8 (m, -$H_{13}$) ; <5 (d, -$H_{27}$) isomer $B_2$ or >5 (d, -$H_{27}$) isomer $B_1$; approximately 5.70 (limiting AB, -$H_{11}$ and -$H_{10}$) ;

approximately 7.7 (>NH at 8); approximately 7.8 (s, -H₂0).

The isomer which has NMR characteristics identical to those stated above for the isomers A₁ and A₂ of the products of general formula (I) is called isomer A of the product of general formula (II), it being understood that the H at 27 is characterized by: 4.7 (d, J≦1 Hz).

The isomer which has NMR characteristics identical to those stated above for the isomers B₁ and B₂ of the products of general formula (I) is called isomer B of the product of general formula (II), it being understood that the H at 27 is characterized by: 4.6 (d, J≧2.5 Hz).

EXAMPLE 1

An aqueous solution (40 cc) of Oxone ® (8.1 g) is added, at 0° C., to 26-[(2-diethylaminoethyl)thio]-pristinamycin II$_B$ (isomer A) (13 g) suspended in distilled Water (170 cc), in the course of 15 minutes. The mixture obtained is stirred for 30 minutes at 0° C. and NORIT SX ULTRA charcoal (1.3 g) and a small amount of sodium thiosulphate are added to it. After stirring for 30 minutes at 20° C., the suspension is filtered through Celite and then rinsed with distilled water (50 cc). The solution is adjusted to pH 7 by adding solid sodium bicarbonate and then washed with dichloromethane (3×100 cc). The organic phases are combined, dried over magnesium sulphate, filtered and then concentrated to dryness under reduced pressure (2.7 kPa) at 30° C. to give a light beige-coloured solid (9.9 g) containing 26-[(2-diethylaminoethyl)sulphinyl]pristinamycin II$_B$ (isomer A₂) (85%), isomer A₁ (10%) and 26-[(2-diethylaminoethyl)sulphonyl]pristinamycin II$_B$ (5%).

The crystalline form of 26-[(2-diethylaminoethyl]sulphinyl]pristinamycin II$_B$ may be obtained by operating as follows:

A part of the solid obtained above (5 g) is taken up with acetonitrile (13 cc). After dissolving in the heated state, ether (10 cc) is added and crystallization is initiated by scratching. The crystals are filtered, washed with ether and then dried under reduced pressure (270 Pa) at 20° C. 26-[(2-Diethylaminoethyl)sulphinyl]pristinamycin II$_B$ (3.9 g) (isomer A₂: 85%, isomer A₁: 15%) in the form of white crystals, m.p. approximately 116° C., is thereby obtained.

NMR spectrum (isomer A₂)
1.03 (t, —N(CH₂CH₃)₂)
1.75 (s, —CH₃ at 33)
2.05 and 2.55 (2m, >CH₂ at 25)
2.45 to 2.70 (m, —N(CH₂CH₃)₂)
2.70 to 3.10 (m,

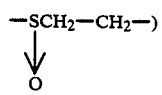

—SCH₂—CH₂—)
↓
O 2.75 (m, H at 4)
2.92 to 3.10 (m, >CH₂ at 15)
3.22 (m, H at 26)
3.82 (s, >CH₂ at 17)
4.81 (d, H at 27)
5.5 (d, H at 13)
6.19 (d, H at 11)
6.50 (dd, >NH at 8)
6.58 (dd, H at 5)
8.12 (s, H at 20)
NMR spectrum (isomer A₁)
1.04 (t, —N(CH₂CH₃)₂)
1.69 (s, —CH₃ at 33)
2 to 2.3 (m, >CH₂ at 25)
2.60 (m, >N-CH₂-CH₃)
2.7 to 2.95 (m, —S(O)-CH₂-CH₂-N<)
2.7 (m, H at 4)
2.86 and 3.04 (2dd, >CH₂ at 15)
3.28 (m, H at 26)
3.78 (AB system, >CH₂ at 17)
5.25 (d, H at 27)
5.4 (d, H at 13)
6.15 (d, H at 11)
6.60 (dd, H at 5)
6.83 (dd, >NH at 8)
8.08 (s, H at 20)

The 26-[(2-diethylaminoethyl)thio]pristinamycin II$_B$ may be prepared as described in U.S. Pat. No. 4,590,004.

EXAMPLE 2

An aqueous solution (10 cc) of Oxone ® (1.9 g) is added, at —5° C., to 26-[(2-diethylaminoethyl)thio]pristinamycin II$_B$ (isomer A) (3 g) suspended in a mixture of distilled water (30 cc) and ethanol (6 cc), in the course of 10 minutes. After stirring for 10 minutes, the reaction mixture is washed with dichloromethane (2×20 cc). The aqueous phase is adjusted to pH 7 by adding solid sodium bicarbonate and then extracted with dichloromethane (4×50 cc). The organic phases are combined, dried over magnesium sulphate, filtered and then concentrated to dryness under reduced pressure (2.7 kPa) at 40° C. A white solid (2.4 g) containing 26-[(2-diethylaminoethyl)sulphinyl]pristinamycin II$_B$ (isomer A₂: 88%, isomer A₁: 6%) and 26-[(2-diethylaminoethyl)sulphonyl]pristinamycin II$_B$ (6%) is thereby obtained. The NMR characteristics of the product obtained are identical to those of the product in Example 1.

EXAMPLE 3

Oxone ® (1.65 g) dissolved in distilled water (32 cc) is added slowly, at —30° C., to 26-{[(R)-1-diethylamino-2-propyl]thio}pristinamycin II$_B$ (isomer A: 87%, B: 13%) (3.2 g) dissolved in methanol (48 cc). After maintaining the mixture at —30° C. for 30 minutes and then at —40° C. for 15 minutes, distilled water (30 cc) followed by NORIT SX ULTRA charcoal (3g) are added. The mixture is stirred for 30 minutes at 20° C., filtered through Celite and then rinsed with distilled water (50 cc). The aqueous phase is washed with ethyl acetate (2×100 cc) and then with ethyl ether (50 cc) before being adjusted to pH 7 by adding solid sodium bicarbonate and then extracted with dichloromethane (2×250 cc). The organic phases are washed with distilled water (50 cc), dried over magnesium sulphate, filtered and then concentrated to dryness under reduced pressure (2.7 kPa) at 30° C. A very light yellow cake (2.4 g) is obtained, which is stirred in a pentane: diethyl ether (50:50 by volume) mixture (40 cc). After filtering and then drying under reduced pressure (270 Pa) at 20° C., 26-{[(R)-1-diethylamino-2-propyl]sulphinyl}pristinamycin II$_B$ (isomer A₂: 80%) (2.2 g) in the form of an off-white solid, m.p. approximately 140° C., is obtained.
NMR spectrum:
1.02 (t, —N(CH₂-CH₃)₂)
1.34 (d,

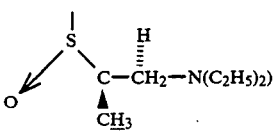

1.72 (s, —CH₃ at 33)
2.01 and 2.55 (2m, >CH₂ at 25)
2.45 to 2.70 (m, 1H in —CH₂-N(CH₂-CH₃)₂ and —N(CH₂-CH₃)₂)
2.90 (m, 1H in —CH₂-N(CH₂CH₃)₂)
2.76 (m, H at 4)
2.88 and 3.08 (2dd, >CH₂ at 15)
3 (m,

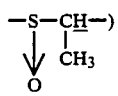

3.73 (m, H at 26)
3.80 (s, >CH₂ at 17)
4.92 (broad s, H at 27)
5.42 (d, H at 13)
6.15 (d, H at 11)
6.55 (dd, H at 5)
6.70 (dd, >NH at 8)
8.06 (s, H at 20)

The 26-{[(R)-1-diethylamino-2-propyl]thio}pristinamycin II_B may be obtained as follows:

(R)-1-Diethylamino-2-propanethiol (3.2 cc) is added, at −30° C., under a nitrogen atmosphere, to pristinamycin II_A (10.5 g) suspended in methanol (200 cc). After stirring for 18 hours at −30° C., methyl acrylate (2 cc) is added and the mixture is stirred for 1 hour. Distilled water (200 cc) potassium hydrogen sulphate (amount required to adjust the pH to 4 at −10° C.) followed by NORIT SX ULTRA charcoal (10 g) are then added. After stirring for 30 minutes at 0° C., the mixture is filtered through Celite and then washed with distilled water (150 cc). The aqueous phase is washed with ethyl acetate (100 cc) and then with ethyl ether (100 cc) and then adjusted to pH 7 by adding solid sodium bicarbonate. After extracting with dichloromethane (200 cc), the organic phase is washed with water (100 cc), dried over magnesium sulphate, filtered and then concentrated to dryness under reduced pressure (2.7 kPa) at 30° C. The solid obtained is crushed in ethyl ether (100 cc), filtered through sintered glass and then dried under reduced pressure (270 Pa) at 20° C. 26-{[(R)-1-Diethylamino-2-propyl]thio}pristinamycin II_B (isomer A: 85%, isomer B: 15%) in the form of a light beige-coloured solid, m.p. approximately 130° C., is thereby obtained.

NMR spectrum (isomer A)

1.03 (t, —N(CH₂CH₃)₂)

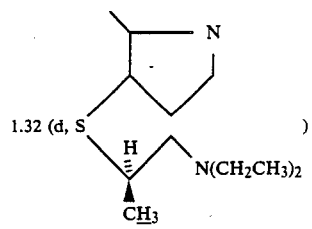

1.72 (s, —CH₃ at 33)
1.88 and 2.10 (2m, >CH₂ at 25)
2.55 (m, —N(CH₂CH₃)₂)
2.45 and 2.60 (2m, —CH₂-N(CH₂CH₃)₂)
2.78 (m, H at 4)
2.92 and 3.10 (2dd, >CH₂ at 15)
3 (m,

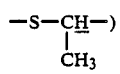

3.52 (m, H at 26)
3.82 (s, >CH₂ at 17)
4.79 (broad s, H at 27)
5.49 (d, H at 13)
6.13 (d, H at 11)
6.32 (c, >NH at 8)
6.52 (dd, H at 5)
8.13 (s, H at 20)
(isomer B)

1 (t, —N(CH₂CH₃)₂)

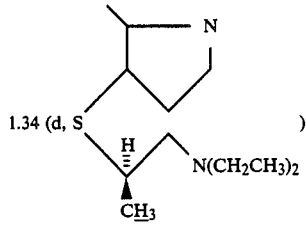

1.50 (s, —CH₃ at 33)
2.05 and 2.5 (2m, CH₂ at 25)
2 5 (m, >N-CH₂-CH₃)
2.44 and 2.55 (2m, —CH₂-N(CH₂CH₃)₂)
2.62 (m, H at 4)
2.74 and 3.10 (2dd, >CH₂ at 15)
3.01 (m,

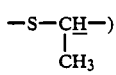

3.69 and 3.89 (2d, >CH₂ at 17)
3.74 (m, H at 26)
4.01 (d, J=2.5, H at 27)
4.80 (AB system, H at 13 and H at 14)
5.65 (d, H at 11)
6.60 (dd, H at 5)
7.71 (m, >NH at 8)
7.80 (s, H at 20)

The (R)-1-diethylamino-2-propanethiol may be prepared as follows:

(R)-N,N-Diethyl-2-mercaptopropionamide (137.5 g) dissolved in ethyl ether (500 cc) is added dropwise to a suspension of lithium aluminium hydride (34.2 g) in ethyl ether (1600 cc) in the course of 1 hour and 20 minutes. The reaction mixture is then maintained under reflux for 2 hours and 30 minutes and then cooled to a temperature in the vicinity of 0° C. Distilled water (40 cc) is then added so that the temperature of the mixture does not exceed 20° C. and 5N sodium hydroxide (29.4 cc) followed by distilled water (133 cc) are then added. The reaction mixture is filtered and the pH of the filtrate is adjusted to 8 by adding acetic acid (70 cc). The mixture obtained is filtered again, rinsed with ethyl ether (3×300 cc) and the filtrate is dried over sodium sulphate, filtered and concentrated to dryness under reduced pressure (2.7 kPa) at a temperature in the vicinity of 30° C. A yellow oil is obtained, which is purified by distillation under reduced pressure (1.3 kPa). (R)-1-Diethylamino-2-propanethiol (101 g) in the form of a colourless oil [b.p.1.3 kPa=55°-56° C.; $[\alpha]_D^{20}=37.1°$ (c=4.8; $CH_3OH$)].

The (R)-N,N-diethyl-2-mercaptopropionamide may be prepared as follows:

(R)-N,N-Diethyl-2-acetylthiopropionamide (105 g) in ethyl ether (600 cc) is added to a 5N sodium hydroxide solution (517 cc) maintained at 20° C., in the course of 30 minutes. The reaction mixture is stirred for 2 hours 30 minutes at a temperature in the vicinity of 20° C. The aqueous phase is separated by decantation.

The pH of the aqueous phase is then adjusted to pH=5-6 by slowly adding acetic acid (140 cc). The mixture obtained is extracted with dichloromethane (300 cc) and then with dichloromethane (200 cc), the combined organic phases are dried DVer sodium sulphate, filtered and then concentrated to dryness under reduced pressure (2.7 kPa) at a temperature in the vicinity of 30° C. (R)-N,N-Diethyl-2-mercaptopropionamide (78.6 g) in the form of a purplishblue oil [$[\alpha]_D^{20}=-21.1°$ (c=3.8; $CH_3OH$)].

The (R)-N,N-diethyl-2-acetylthiopropionamide may be prepared as follows:

(S)-N,N-Diethyl-2-chloropropionamide (88.3 g) dissolved in ethanol (150 cc) is added to a suspension of the potassium salt of thiolacetic acid (72.6 g) in ethanol (300cc). The reaction mixture is then heated for 2 hours at a temperature in the vicinity of 60° C. and then filtered and concentrated to dryness under reduced pressure (130 Pa) at a temperature in the vicinity of 50° C. The residue obtained is taken up and stirred in dichloromethane (500 cc) and then washed with distilled water (300 cc), with a 10% aqueous potassium bicarbonate solution (300 cc) and then with distilled water (300 cc). The organic phase is decanted, dried over sodium sulphate and charcoal 3S (1 g) filtered and then concentrated to dryness under reduced pressure (2.7 kPa) at a temperature in the vicinity of 30° C. The residue obtained is distilled under reduced pressure (17 Pa). (R)-N,N-Diethyl-2-acetylthiopropionamide (105.5 g) in the form of a slightly yellow oil [b.p.17 Pa=105°-107° C.; $[\alpha]_D^{20}=+156°$ (c=18.1; $CHCl_3$)] is thereby obtained.

The (S)-N,N-diethyl-2-chloropropionamide may be obtained as follows:

Diethylamine (480 cc) is added to a solution of (S)-2-chloropropionyl chloride (175.2 g) in chloroform (900 cc), which is maintained at 0° C., in the course of 1 hour. Distilled water (400 cc) and dichloromethane (300 cc) are added to the reaction mixture. The organic phase is decanted and then washed with an aqueous 2N hydrochloric acid solution (300 cc) and then with distilled water (400 cc). The organic phase is dried over sodium sulphate, filtered and then concentrated to dryness under reduced pressure (2.7 kPa) at a temperature in the vicinity of 30° C. The residue obtained is distilled under reduced pressure (17 Pa). (S)-N,N-Diethyl-2-chloropropionamide (161.9 g) in the form of a colourless oil [b.p.17 Pa=83°-85° C.; $[\alpha]_D^{20}=+39.7°$(c=10.4; $CHCl_3$)] is thereby obtained.

(R)- and (S)-2-chloropropionyl chlorides may be prepared according to the method described by S-C. J. FU, S. M. BIRNBAUM and J. P. GREENSTEIN, J. Am. Chem. Soc., 76, 6054 (1954).

EXAMPLE 4

An aqueous solution (20 cc) of Oxone ® (1.01 g) is added, at −60° C., to 26-{[(S)-1-diethylamino-2-propyl]thio}pristinamycin $II_B$ (isomer A) (2 g) dissolved in methanol (30 cc), in the course of 30 minutes. The suspension obtained is stirred for 30 minutes at −60° C. and then for 16 hours at −20° C. Oxone ® (0.2 g) dissolved in water (5 cc) is then added and the mixture is stirred for 30 minutes at −20° C. The reaction mixture is diluted with water (100 cc), treated with NORIT SX ULTRA charcoal (0.5 g), stirred for 15 minutes, filtered through celite and then rinsed with water (3×5 cc). The aqueous phase is extracted with ethyl acetate (3×50 cc), adjusted to pH 7 by adding solid sodium bicarbonate, saturated with sodium chloride and then washed with dichloromethane (3×50 cc).

The organic phases are combined, dried over magnesium sulphate, filtered and then concentrated to dryness under reduced pressure (2.7 kPa) at 30° C. A white cake is thereby obtained, which is stirred in diethyl ether (20 cc) The resulting solid is filtered and then dried under reduced pressure (270 Pa) at 20° C. to give 26-{[(S)-1-diethylamino-2-propyl]sulphinyL}pristinamycin $II_B$ (isomer $A_2$: 90%, isomer $A_1$: 5%) (1.5 g) in the form of a whitish solid, m.p. approximately 130° C., the NMR characteristics of which are identical to those of the product obtained in Example 5 below.

The 26-{[(S)-1-diethylamino-2-propyl]thio}pristinamycin $II_B$ (isomer A) may be obtained as follows:

(S)-1-Diethylamino-2-propanethiol (3.2 g) is added, at −20° C., to pristinamycin $II_A$ (10.5 g) dissolved in a methylene chloride : methanol (50:50 by volume) mixture, under a nitrogen atmosphere. After stirring for 70 hours at −20° C., the reaction mixture is concentrated to dryness under reduced pressure (2.7 kPa) at 30° C. and then taken up with ethyl acetate (100 cc). The solution obtained is washed with an aqueous 0.2N potassium hydrogen sulphate solution (100 cc). The aqueous phase is decanted and then washed with ethyl acetate (3×100 cc). The organic phase is washed with distilled water (50 cc) and the aqueous phases are then combined, adjusted to pH 7 by adding solid sodium bicarbonate (2 g) and washed with dichloromethane (100 cc followed by 2×50 cc). The latter organic phases are combined, dried over sodium sulphate, filtered and then concentrated to dryness under reduced pressure (2.7 kPa) at 30° C. The solid obtained is stirred in ethyl ether (150 cc), filtered and then rinsed with ether (3×10 cc). A beige-coloured solid (9.2 g) is thereby obtained, which is recrystallized in acetonitrile (20 cc). After filtering, drying at 20° C. under reduced pressure (270 Pa), 26-{[(S)-1-diethylamino-2-propyl]thio}-pristinamycin $II_B$ (isomer A) (2.3 g) in the form of white crystals, m.p. approximately 128° C., is obtained.

NMR spectrum
1.04 (t, —N(CH$_2$CH$_3$)$_2$)
1.39 (d,

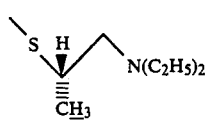

1.73 (s, —CH$_3$ at 33)
1.90 and 2.13 (2m, >CH$_2$ at 25)
2.4 to 2.7 (m, —CH$_2$—N(CH$_2$CH$_3$)$_2$)
2.78 (m, H at 4)
2.93 and 3.12 (2dd, >CH$_2$ at 15)
3.02 (m,

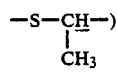

3.55 (m, H at 26)
3.84 (s, >CH$_2$ at 17)
4.81 (broad s, H at 27)
5.49 (d, H at 13)
6.15 (d, H at 11)
6.30 (c, >NH at 8)
6.53 (dd, H at 5)
8.13 (s, H at 20)

The (S)-1-diethylamino-2-propanethiol may be prepared as follows:

(S)-N,N-Diethyl-2-mercaptopropionamide (171 g) dissolved in ethyl ether (500 cc) is added dropwise to a suspension of lithium aluminium hydride (42.6 g) in ethyl ether (1500 cc) in the course of 1 hour and 20 minutes. The reaction mixture is then maintained under reflux for 2 hours and 30 minutes and then cooled to a temperature in the vicinity of 0° C. Distilled water (49.8 cc) is then added so that the temperature of the mixture does not exceed 20° C., and 5N sodium hydroxide (36.6 cc) and distilled water (166 cc) are then added. The reaction mixture is filtered, the pH of the filtrate is adjusted to 8 by adding acetic acid (70 cc). The mixture obtained is filtered again, the filtrate is dried over sodium sulphate, filtered and then concentrated to dryness under reduced pressure (2.7 kPa) at a temperature in the vicinity of 30° C. A yellow oil is obtained, which is purified by distillation under reduced pressure (1.3 kPa). (S)-1-Diethylamino-2-propanethiol (100 g) in the form of a colourless oil [b.p.1.3 kPa=55°-56° C.; $[\alpha]_D^{20}$=+39.6° (c=5.6, CH$_3$OH)] is thereby obtained.

The (S)-N,N-diethyl-2-mercaptopropionamide may be prepared as follows:

(S)-N,N-diethyl-2-acetylthiopropionamide (223 g) in ethyl ether (1000 cc) is added to a 5N sodium hydroxide solution (1100 cc) which is maintained at 20° C., in the course of 30 minutes. The reaction mixture is stirred for 20 hours at a temperature in the vicinity of 20° C. The aqueous phase is separated by decantation and then washed with ethyl ether (3×250 cc). The pH of the aqueous phase is then adjusted to 5 by slowly adding acetic acid (280 cc). The mixture obtained is extracted with dichloromethane (500 cc followed by 2×250 cc), the combined organic phases are dried over sodium sulphate in the presence of carbon black, filtered and then concentrated to dryness under reduced pressure (2.7 kPa) at a temperature in the vicinity of 30° C. (S)-N,N-Diethyl-2-mercaptopropionamide (171.7 g) in the form of a purplish-blue oil [[$\alpha]_D^{20}$=+20.7° C. (c=3, CH$_3$OH)] is thereby obtained.

The (S)-N,N-diethyl-2-acetylthiopropionamide may be prepared as follows:

(R)-N,N-Diethyl-2-chloropropionamide (20 g) dissolved in ethanol (30 cc) is added to a suspension of the potassium salt of thiolacetic acid (16 g) in ethanol (70 cc). The reaction mixture is then heated for 2 hours at a temperature in the vicinity of 55° C. and then concentrated to dryness under reduced pressure (130 Pa) at a temperature in the vicinity of 60° C. The residue obtained is crushed in dichloromethane (300 cc) and then washed with distilled water (200 cc). The organic phase is decanted, dried over sodium sulphate, filtered and then concentrated to dryness under reduced pressure (2.7 kPa) at a temperature in the vicinity of 30° C. The residue obtained is distilled under reduced pressure (17 Pa). (S)-N,N-Diethyl-2-acetylthiopropionamide (22 g) in the form of a slightly yellow oil [b.p.$_{17 Pa}$=105°-107° C.; $[\alpha]_D^{20}$=−169° (c=10; CHCl$_3$)] is thereby obtained.

The (R)-N,N-diethyl-2-chloropropionamide may be prepared as follows:

Diethylamine (153 g) is added to a solution, maintained at 20° C., of (R)-2-chloropropionyl chloride (87.7 g) in chloroform (600 cc), in the course of 1 hour. The reaction mixture is washed with distilled water (500 cc), with an aqueous 1N hydrochloric acid solution (3×500 cc) and then with distilled water (500 cc). The organic phase is dried over sodium sulphate, filtered and then concentrated to dryness under reduced pressure (2.7 kPa) at a temperature in the vicinity of 30° C. The residue obtained is distilled under reduced pressure (17 Pa). (R)-N,N-Diethyl-2-chloropropionamide (43 g) in the form of a colourless oil [b.p.$_{17\ Pa}$=75°-80° C.; $[\alpha]_D^{20}$=−43.3° (c=10; CHCl$_3$)] is thereby obtained.

EXAMPLE 5

(S)-1-Diethylamino-2-propanethiol (17.6 g) is added, at −38° C., to a suspension of pristinamycin II$_A$ (63 g) in methanol (630 cc), in the course of 30 minutes, under a nitrogen atmosphere. After stirring for 20 hours, distilled water (150 cc) is added followed by the addition of an aqueous solution (410 cc) of Oxone ® (33.6 g) in the course of 30 minutes, at a temperature of −38° C. The suspension obtained is stirred for 1 hour at −38° C., treated with sodium thiosulphate (1.2 g), filtered at 20° C. through sintered glass and then washed with distilled water (3×200 cc). NORIT SX ULTRA charcoal (20 g) is added to the aqueous phase and the suspension is stirred for 30 minutes and then filtered through Celite, washing the filtrate with distilled water (3×200 cc). The solution is adjusted to pH 7 with solid sodium bicarbonate (15 g) and then washed with dichloromethane (3×500 cc). The organic phases are combined, dried over sodium sulphate, filtered and then concentrated to dryness under reduced pressure (2.7 kPa) at 30° C. A beige-coloured cake (55 g) is obtained, which is stirred in ethyl ether (500 cc). After filtering, washing with ethyl ether (3×50 cc) and then drying under partial vacuum (270 Pa) at 20° C., a white solid (46.6 g) is obtained, which is dissolved in a dichloromethane:methanol (98:2 by volume) mixture (150 cc) and acetic acid (4 cc) is then added to it. This solution is purified by flash chromatography [eluant: dichloromethane:methanol (98:2 by volume)], collecting 100-cc fractions. After concentration under reduced pressure (2.7 kPa) at 30° C., a solid (36 g) is obtained, which is dissolved in distilled water (400 cc) to which potassium hydrogen sulphate (6.5 g) has been added. The solution is washed with ethyl acetate (4×500 cc), adjusted to pH 7 by adding solid sodium bicarbonate (5 g) and then extracted with dichloromethane (200 cc followed by 2×150 cc). The organic phases are combined, dried over magnesium sulphate, filtered and then concentrated to dryness under reduced pressure (2.7 kPa) at 30° C. to give a beige-coloured cake (33.8 g), which is stirred in ethyl ether (300 cc). After filtering, 26-{[(S)-1-diethylamino-2-propyl]sulphinyl}pristinamycin II$_B$ (isomer A$_2$) (29.3 g) in the form of a pale yellow powder, m.p. approximately 140° C., is isolated.

NMR spectrum (isomer A$_2$)
1.05 (t, —N(CH$_2$—CH$_3$)$_2$)
1.27 (d,

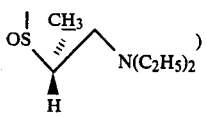

1.74 (s, —CH$_3$ at 33)
2.10 (m, 1H in >CH$_2$ at 25)
2.45 to 2.70 (m, 1H in >CH$_2$ at 25, 1H in >CH$_2$—N(CH$_2$CH$_3$)$_2$, —N(CH$_2$CH$_3$)$_2$)
2.80 (m, H at 4)
2.88 (m, 1H in >CH$_2$—N(CH$_2$CH$_3$)$_2$)
2.90 and 3.15 (2dd, >CH$_2$ at 15)
3.06 (m,

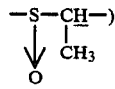

3.41 (m, H at 26)
3.83 (s, >CH$_2$ at 17)
4.77 (broad s, H at 27)
5.50 (d, H at 13)
6.20 (d, H at 11)
6.55 (m, >NH at 8)
6.63 (dd, H at 5)
8.11 (s, H at 20)

EXAMPLE 6

Oxone ® (30.7 g) dissolved in distilled water (140 cc) is added, at 0° C., to 26-[(2-diethylaminoethyl)thio]pristinamycin II$_B$ (50 g) in dichloromethane (200 cc) and distilled water (250 cc), in the course of 20 minutes. After stirring for 10 minutes, the organic phase is decanted, the aqueous phase is washed with dichloromethane (100 cc) and then adjusted to pH 7 by adding a saturated sodium bicarbonate solution (120 cc). The aqueous phase is washed with dichloromethane (5×100 cc), while adjusting the pH to 7 at each washing by adding sodium bicarbonate. The organic phases are combined, dried over magnesium sulphate, filtered and then concentrated to dryness under reduced pressure (2.7 kPa) at 40° C. 26-[(2-Diethylaminoethyl)sulphinyL]pristinamycin II$_B$ (isomer A$_2$: 85%, isomer A$_1$: 10%) (31 g) in the form of a light beige-coloured powder, the characteristics of which are identical to those of the product obtained in Example 1, is thereby obtained.

EXAMPLE 7

Concentrated sulphuric acid (0.08 cc), followed by Oxone ® (0.9 g) dissolved in distilled water (10 cc) are added slowly at 0° C. to [(S)-1-diethylamino-2propyl]-26-thiopristinamycin II$_B$ (isomer A) (2 g) dissolved in ethanol (30 cc) and water (20 cc). The solution obtained is stirred for 4 hours at 20° C. Solid sodium bicarbonate is then added to a pH of 4 and stirring is continued for 2 days at 20° C. Distilled water (25 cc) and Norit SX Ultra black (2 g) are then added. The mixture is filtered through Celite, is rinsed with dichloromethane (20 cc) and is then adjusted to pH 7 with solid sodium bicarbonate.

The aqueous phase is separated off and is then washed with dichloromethane (2×25 cc). The organic phases are dried over magnesium sulphate, are filtered, and are then concentrated to dryness under reduced pressure (2.7 kPa) at 40° C.

A beige-coloured solid (1.6 g) is obtained in this manner, containing 80% of [(S)-1-diethylamino-2-propyl]-26-sulphinylpristinamycin II$_B$ (isomer A$_2$), 10% of isomer A$_1$ and 10% of the initial sulphide and whose characteristics are identical with those described in Example 4.

EXAMPLE 8

Concentrated sulphuric acid (0.24 cc) followed, slowly, by Oxone ® (2.7 g) dissolved in distilled water (10 cc) is added to [(S)-1-diethylamino-2-propyl]-26-thiopristinamycin II$_B$ (isomer A) (6 g) dissolved in distilled water (20 cc) and methanol (90 cc) and cooled to −30° C. The turbid solution obtained is stirred at −30° C. for 1 hour. Norit SX Ultra black (0.6 g ) is then added and the mixture is then filtered through Celite. The filtrate is adusted to pH 7 by the addition of solid sodium bicarbonate and is then washed with dichloromethane (3×50 cc). The organic phases are combined, are dried over magnesium sulphate and filtered and are then concentrated to dryness under reduced pressure (2.7 kPa) at 30° C.

The resultant solid is stirred in a mixture of ethyl acetate (20 cc) and ethyl ether (70 cc), is filtered off and is then washed with ethyl ether (50 cc). A light-beige solid (4.6 g) is thus obtained and is purified by flash chromatography [eluent: ethyl acetate-methanol (90-10 by volume)], 15-cc fractions being collected. After fractions 47 to 54 have been concentrated to dryness under reduced pressure (2.7 kPa) at 30° C., [(S)-1-diethylamino-2-propyl]-26-sulphinylpristinamycin II$_B$ (isomer A$_2$) (1.7 g) is obtained, containing 10% of the starting sulphide and having characteristics which are identical to the product described in Example 4.

EXAMPLE 9

Distilled water (200 cc) followed, slowly, by Oxone ® (15.1 g) dissolved in distilled water (70 cc) are added to [(2S)-2-diethylaminopropyl]-26-thiopristinamycin II$_B$ (25.5 g) dissolved in ethanol (350 cc), at −30° C. After 1 hour 30 minutes' stirring at −30° C., sodium thiosulphate (3.7 g) is added as a solution in water (20 cc). The reaction mixture is then poured into distilled water (400 cc) and dichloromethane (200 cc), and adjusted to pH 7 with sodium bicarbonate. The organic phase is separated off and the aqueous phase is washed with dichloromethane (3×200 cc). The organic phases are combined, dried over magnesium sulphate, filtered and then concentrated to dryness under reduced pressure (2.7 kPa) at 30° C. A light-yellow solid (24 g) is thus obtained and is purified by flash chromatography [eluent: chloroform-methanol (90-10 by volume)]. After fractions 23 to 28 (50-cc volume) have been concentrated to dryness under reduced pressure (2.7 kPa) at 30° C., a yellow solid foam is obtained, which is stirred with ethyl ether (100 cc) and filtered off and then dried under reduced pressure (90 Pa) at 20° C. [(2S)-2-Diethylaminopropyl]-26-sulphinylpristinamycin II$_B$ (isomer A$_2$) (11.3 g) is obtained in this manner in the form of a light-yellow powder melting at about 128° C.

NMR spectrum 1.1 (m, —CH$_2$CH$_3$ and

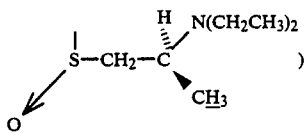

1.77 (s, —CH$_3$ at 33)
2 (m, 1H of —CH$_2$— at 25)
2.30 to 2.7 (m, 1H of —CH$_2$— at 25,

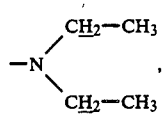

1H of —SO—CH$_2$—)
2.97 (m, 1H of —SO—CH$_2$—)
2.78 (m, >CH— at 4)
2.92 and 3.10 (2 dd, —CH$_2$— at 15)
3.13 (m, >CH— at 26)
3.50 (m, >N—CH—)
3.81 (s, —CH$_2$— at 17)
4.77 (d, >CH— at 27)
5.52 (d, =CH— at 13)
6.18 (d, =CH— at 11)
6.48 (m, —NH— at 8)
6.57 (dd, =CH— at 5)
8.12 (s, =CH— at 20)

[(2S)-2-Diethylaminopropyl]-26-thiopristinamycin II$_B$ (isomer A) may be obtained in the following manner:

(S)-2-Diethylaminopropanethiol (10 g) dissolved in chloroform (50 cc) is added to pristinamycin II$_A$ (31.5 g) dissolved in methanol (230 cc) and chloroform (70 cc), cooled to −40° C. under a nitrogen atmosphere. After 4 days' stirring at −40° C., the mixture is concentrated to dryness under reduced pressure (2.7 kPa) at 35° C. and the resultant solid is then stirred with ethyl ether (500 cc), is filtered off and is again stirred with diethyl ether (300 cc). After being filtered off, the solid is dried (90 Pa) at 20° C. and is then purified by flash chromatography (eluent: chloroform-methanol (90-10 by volume)], 100-cc fractions being collected. After fractions 18 to 30 have been concentrated to dryness under reduced pressure (2.7 kPa) at 30° C., [(2S)-2-diethylaminopropyl]-26thiopristinamycin II$_B$ (isomer A) (26.6 g) is obtained in the form of a light-yellow solid melting at about 110° C.

NMR spectrum:

1.05 (m, CH$_3$—CH$_2$— and

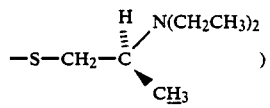

1.72 (s, —CH$_3$ at 33)
1.95 to 2.10 (m, —CH$_2$— at 25)
2.50 (m,

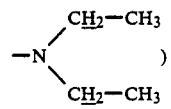

2.60, 2.87 and 3.04 (m, —S—CH$_2$—CH<)
2.77 (m, >CH— at 4)
2.9 and 3.10 (2dd, —CH$_2$— at 15)
3.35 (m, >CH— at 26)
3.82 (s, —CH$_2$— at 17)
4.7 (d, >CH— at 27)
5.47 (d, =CH— at 13)
6.15 (d, =CH— at 11)
6.46 (c, —NH— at 8)
6.54 (dd, =CH— at 5)

(S)-2-Diethylaminopropanethiol may be prepared in the following manner:

A 5N aqueous sodium hydroxide solution (59.4 cc) is added to (S)-2-diethylaminopropylisothiouronium dihydrochloride (39 g) in ethyl ether (140 cc). After 30 minutes' stirring under a nitrogen atmosphere, the aqueous phase is separated off and is then washed with ethyl ether (3×150 cc). The organic phases are combined, are dried over magnesium sulphate and are filtered and then concentrated to dryness under reduced pressure (2.7 kPa) at 30° C. The liquid obtained is distilled at 78° C. at 2.7 kPa to give (S)-2-diethylaminopropanethiol (10.6 g) in the form of a colourless liquid (containing 6% of 1-diethylaminopropanethiol), $[\alpha]_D^{20} = +32 \pm 0.6$ (c=0.943; ethanol).

(S)-2-Diethylaminopropylisothiouronium dihydrochloride may be prepared in the following manner:

A solution of (S)-2-diethylamino-1-chloropropane hydrochloride (45 g) in N,N-dimethylformamide (150 cc) is added to thiourea (18.2 g) dissolved in N,N-dimethylformamide (80 cc), at 130° C. After 5 minutes at 130° C. the solution is cooled. The crystals obtained are filtered off, are washed with ethyl ether and are then dried under reduced pressure (90 Pa) at 20° C. (S)-2-diethylaminopropylisothiouronium dihydrochloride (39 g) is thus obtained in the form of white crystals melting at 209° C. $[\alpha]_D^{20} = -2.6$ (c=1; ethanol).

(S)-2-Diethylamino-1-chloropropane hydrochloride may be prepared in the following manner:

(S)-2-Diethylaminopropanol hydrochloride (50 g) is added in small portions to thionyl chloride (110 cc) at 2° C. The solution obtained is then heated to 60° C. for 4 hours. Excess thionyl chloride is removed by distillation under reduced pressure (90 kPa) and ethyl ether (250 cc) is then added to the residue obtained. The resultant solid is filtered off, is rinsed with ethyl ether (300 cc) and is then recrystallized from methyl isobutyl ketone (150 cc). After filtration and washing with ethyl ether, (S)-2-diethylamino-1-chloropropane hydrochloride (45.6 g) is obtained in the form of white crystals melting at 103° C., $[\alpha]_D^{20} = 0$ (c=0.7; ethanol).

(S)-2-Diethylaminopropanol hydrochloride may be prepared in the following manner:

(S)-N-Acetyl-N-ethyl-2-aminopropanol (48.66 g) dissolved in tetrahydrofuran (300 cc) is added over 20 minutes to a suspension of lithium aluminium hydride (18.23 g) in tetrahydrofuran (2000 cc). The reaction mixture is then refluxed for 4 hours and is then cooled to 0° C. Distilled water (22 cc) is then added slowly, followed by 5N aqueous sodium hydroxide solution (16 cc) and distilled water (72 cc). After 1 hour's stirring at 20° C. the mixture is filtered through Celite. The filtrate is concentrated to dryness under reduced pressure (2.7 kPa) at 30° C., is taken up with dichloromethane (300 cc), is dried over magnesium sulphate and is filtered and then concentrated to dryness under reduced pressure (2.7 kPa) at 30° C. to give a light-yellow liquid (42.45 g), which is distilled under reduced pressure. (S)-2-Diethylaminopropanol (26.56 g) is thus obtained in the form of a colourless liquid. [B.p.$_1$ $_{kPa}$=55.5° C.].

(S)-2-Diethylaminopropanol hydrochloride (31.41 g) is obtained in the form of a white solid melting at 98° C. after filtration of the crystals produced by adding a 4.94N solution of hydrochloric acid in ethyl ether (40.5 cc) to the above product dissolved in acetone (136 cc).

$[\alpha]_D^{20}= +20.7$ (c=1; ethanol).

(S)-N-Acetyl-N-ethyl-2-aminopropanol may be obtained in the following manner:

Triethylamine (13.7 cc) is added to (S)-N-ethyl-2-aminopropanol (9.15 g) dissolved in dichloromethane (100 cc), at 0° C., and acetyl chloride (7.1 cc) is then added over 45 minutes. Once the addition is complete the temperature is allowed to return to 20° C. The reaction mixture is diluted with water (100 cc) is adjusted to pH 9 by adding sodium carbonate and is then washed with dichloromethane (2×200 cc). The organic phases are combined, are dried over magnesium sulphate, and are filtered and then concentrated to dryness under reduced pressure (2.7 kPa) at 30° C. to give a yellow liquid (9.54 g) which is distilled at 108±2° C. under reduced pressure (26.3 Pa). A colourless liquid (6 g) is thus obtained, which contains approximately 80% of (S)-N-acetyl-N-ethyl-2-aminopropanol and 20% of the corresponding diacetyl derivative (employed as such in the following synthesis).

(S)-N-Ethyl-2-aminopropanol may be prepared in the following manner:

Ethyl (S)-2-acetylaminopropionate (227 g) in tetrahydrofuran (800 cc) is added over 45 minutes to a suspension of lithium aluminum hydride (81 g) in tetrahydrofuran (4000 cc) at 0° C. Once the addition is complete the temperature is raised to 20° C. and the mixture is then heated under reflux for 5 hours. After cooling to 0° C., distilled water (97 cc) is added slowly, followed by a 5N aqueous sodium hydroxide solution (72 cc) and, finally, distilled water (320 cc). The mixture is filtered at 20° C. through Celite. The filtrate is concentrated to dryness under reduced pressure (2.7 kPa) at 30° C., is taken up with dichloromethane (500 cc), is dried over magnesium sulphate, and is filtered and then concentrated to dryness under reduced pressure (2.7 kPa) at 30° C., to give a yellow liquid (143 g). After distillation under reduced pressure (460 Pa) at 57° C., (S)-N-ethyl-2-aminopropanol (90.8g) is obtained in the form of a colourless liquid.

$[\alpha]_D^{20}= +45.4$ (c=1.48; ethanol).

Ethyl 2-acetylaminopropionate may be prepared as described by J. P. WOLFF III et al., Biochemistry 2, 493 (1963).

We claim:

1. A process for the preparation of a pristinamycin II$_B$ of formula:

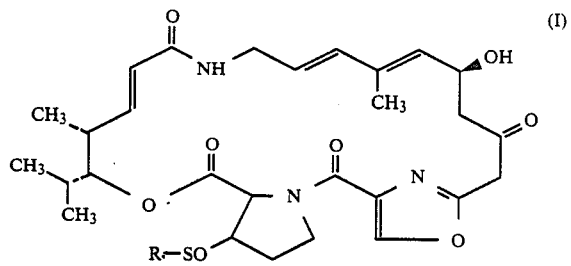

in which R represents
either a heterocyclic radical chosen from 3-azetidinyl, 3-pyrrolidinyl, 3- or 4-piperidyl, or 3- or 4-azepinyl, and unsubstituted or substituted by alkyl,
or alkyl of 2 to 4 carbon atoms, substituted by 1 or 2 radicals chosen from phenyl, cycloalkylamino having 3 to 6 ring carbon atoms or N-alkyl-N-cycloalkylamino having 3 to 6 ring carbon atoms, alkylamino, dialkylamino or dialkylcarbamoyloxy (the alkyl parts of these last 2 radicals being optionally joined to form, with the nitrogen atom to which they are attached, a heterocyclic radical chosen from 1-azetidinyl, 1-pyrrolidiyl, piperidino, 1-azepinyl, morpholino, thiomorpholino in the sulphoxide or sulphone form, 1-piperazinyl, 4-alkyl-1-piperazinyl, N-alkyl-1-homopiperazinyl, or 1-imidazolyl, and unsubstituted or substituted by alkyl) or a said alkyl substituted by a heterocyclic radical chosen from 2-azetidinyl, 2-pyrrolidinyl, 2-piperidyl, 2-azepinyl, piperazinyl, 4-alkyl-piperazinyl, quinolyl, isoquinonlyl, or imidazolyl, and unsubstituted or substituted by alkyl, the said heterocyclic radicals being attached to the alkyl via a carbon atom, at least one of the substituents carried by the alkyl being a nitrogen-containing substituent capable of forming salts,
or a (S)-1-methyl-2-pyrrolidinyl)methyl radical, the aforesaid alkyl radicals being straight-chain or branched and containing, unless otherwise stated, 1 to 10 carbon atoms each, including isomeric forms thereof and mixtures thereof, and its acid addition salts, which comprises oxidizing a pristinamycin II$_B$ (or a salt or protected form thereof) of formula:

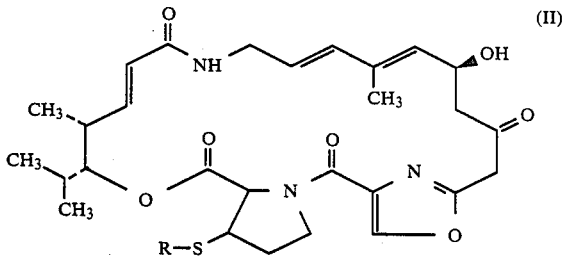

in which R is as defined above, it being understood that where R contains a thiomorpholino radical, the sulphur atom may be in the form of sulphide, sulphoxide or sulphone, with potassium peroxymonosulphate, and optionally separating the product obtained into its isomers and, if necessary, removing any protective radical and optionally converting the product obtained into an acid addition salt.

2. Process according to claim 1 in which the oxidation is carried out in an aqueous medium at $-60°$ to $+25°$ C.

3. Process according to claim 1 in which R is alkyl of 2 to 4 carbon atoms substituted by dialkylamino in which each alkyl has 1 to 4 carbon atoms.

* * * * *